(12) United States Patent
Reitz et al.

(10) Patent No.: US 10,524,730 B2
(45) Date of Patent: Jan. 7, 2020

(54) MEDICAL DEVICES WITH MICRONEEDLE ARRAYS AND METHODS FOR OPERATING SUCH MEDICAL DEVICES

(71) Applicant: MEDTRONIC MINIMED, INC., Northridge, CA (US)

(72) Inventors: James A. Reitz, Simi Valley, CA (US); Raymond M. Russell, Arcadia, CA (US); Anthony C. Cannistraci, Sylmar, CA (US); David Pavell, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 196 days.

(21) Appl. No.: 15/719,359

(22) Filed: Sep. 28, 2017

(65) Prior Publication Data

US 2019/0090811 A1   Mar. 28, 2019

(51) Int. Cl.
*A61B 5/00* (2006.01)
*A61B 5/145* (2006.01)
*A61M 37/00* (2006.01)
*B21D 22/28* (2006.01)

(52) U.S. Cl.
CPC .......... *A61B 5/685* (2013.01); *A61B 5/14514* (2013.01); *A61B 5/14532* (2013.01); *A61M 37/0015* (2013.01); *A61M 2037/0023* (2013.01); *A61M 2037/0053* (2013.01); *B21D 22/28* (2013.01)

(58) Field of Classification Search
CPC .......... A61M 37/0015; A61M 5/14248; A61M 5/1723; A61M 5/425; A61M 5/2033; A61B 5/150099; A61B 17/205; A61B 5/14532; A61B 5/6849; A61B 5/1473; A61B 5/150984; A61B 5/685; A61B 5/14514; B81C 1/00111; B81C 99/0085; A61N 1/325; A61N 1/30; A61K 9/0021; A61J 1/06; B29C 33/3885; B29C 67/00; B29C 51/082; A61L 27/28
See application file for complete search history.

(56) References Cited

U.S. PATENT DOCUMENTS

| 4,562,751 | A | 1/1986 | Nason et al. |
| 4,685,903 | A | 8/1987 | Cable et al. |
| 4,755,173 | A | 7/1988 | Konopka et al. |
| 5,080,653 | A | 1/1992 | Voss et al. |

(Continued)

*Primary Examiner* — Manuel A Mendez
(74) *Attorney, Agent, or Firm* — Lorenz & Kopf, LLP (57) ABSTRACT

Microneedle arrays, methods for fabricating microneedle arrays, medical devices, and methods for operating medical devices are provided. A method for fabricating a microneedle array includes providing a sheet blank of material. Further, the method includes stamping the sheet blank of material with a progression of dies, wherein the material is displaced into the microneedle array. A medical device includes a microneedle array, a base member having a first surface supporting the microneedle array and a second surface, and a flexible wall enclosing a chamber between the flexible wall and the second surface of the base member. The flexible wall is biased toward an extended configuration enclosing a first volume in the chamber. Further, the flexible wall is movable to a depressed configuration enclosing a second volume in the chamber less than the first volume.

20 Claims, 10 Drawing Sheets

(56) References Cited

U.S. PATENT DOCUMENTS

| | | |
|---|---|---|
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,344,499 B1 * | 3/2008 | Prausnitz ........... A61M 37/0015 600/309 |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2002/0016562 A1 * | 2/2002 | Cormier ............ A61M 37/0015 604/20 |
| 2007/0004989 A1 * | 1/2007 | Dhillon ............. A61M 37/0015 600/583 |
| 2007/0123819 A1 | 5/2007 | Mernoe et al. |
| 2010/0160861 A1 | 6/2010 | Causey, III et al. |
| 2013/0158468 A1 * | 6/2013 | Bernstein ......... A61B 5/150022 604/27 |

* cited by examiner

MEDICAL DEVICES WITH MICRONEEDLE ARRAYS AND METHODS FOR OPERATING SUCH MEDICAL DEVICES

TECHNICAL FIELD

Embodiments of the subject matter described herein relate generally to medical devices, and more particularly, embodiments of the subject matter relate to devices for transferring fluids through a patient's skin.

BACKGROUND

Active agents (or drugs) are conventionally administered either orally or by injection. Unfortunately, many agents can be ineffective or have radically reduced efficacy when orally administered since they either are not absorbed or are adversely affected before entering the bloodstream and thus do not possess the desired activity. Further, orally administered agents may not take effect as quickly as injected agents. On the other hand, the direct injection of the agent into the bloodstream, while assuring no modification of the agent during administration, is a difficult, inconvenient, painful and uncomfortable procedure which sometimes results in poor patient compliance.

Transdermal delivery can provide a method of administering active agents that would otherwise need to be delivered via hypodermic injection or intravenous infusion. In addition, transdermal delivery, when compared to oral delivery, avoids the harsh environment of the digestive tract, bypasses gastrointestinal drug metabolism, reduces first-pass effects, and avoids the possible deactivation by digestive and liver enzymes.

In some cases, however, the delivery of active agents using transdermal delivery can be limited by the barrier properties of skin. The main barrier to the transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which make up the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Microneedle or micro-pin arrays provide intradermal delivery of active agents, which otherwise would not penetrate the stratum corneum. The sharp microneedle tip is designed to be able to penetrate the stratum corneum layer of the skin, but short enough not to puncture nerve endings, thus reducing or eliminating pain upon insertion. However, the penetration of microneedles to precise levels within the skin tissue and with good reproducibility is often a challenging task. Further, the fabrication of microneedle arrays is generally a time-consuming and costly process, resulting in relatively expensive medical devices.

Accordingly, there is a need to provide a less expensive and highly reproducible method for fabricating microneedle arrays. Further, there is a need to provide microneedle arrays having precisely formed and precisely located microneedles. Further, there is a need to provide a medical device incorporating a microneedle array to transfer fluid through a patient's skin. Also, there is a need for an improved method for operating a medical device by transferring fluid utilizing a microneedle array. Fabrication methods, microneedle arrays, medical devices and methods for operating medical devices that satisfy the various requirements that may be imposed.

BRIEF SUMMARY

Methods for fabricating microneedle arrays, microneedle arrays, medical devices, and methods for operating a medical device are provided. An exemplary method for fabricating a microneedle array includes providing a sheet blank of material and stamping the sheet blank of material with a progression of dies to displace the material into a plurality of microneedles forming the microneedle array.

Another method is provided for fabricating a deep drawn microneedle array and includes providing a sheet blank of material and reverse drawing the sheet blank of material to form the microneedle array comprising microneedles extending up from a base member. The height of the microneedles above the base member is greater than the thickness of the base member.

In another embodiment, a microneedle array is provided. The microneedle array includes a one-piece planar base member having an upper surface and a thickness. Further, the microneedle array includes needles formed from and unitary with the planar base member. The needles terminate at a height above the upper surface that is greater than the thickness of the base member.

Another embodiment includes a medical device. The medical device includes a microneedle array. Further, the medical device includes a base member having a first surface supporting the microneedle array and a second surface. Also, the medical device includes a flexible wall enclosing a chamber between the flexible wall and the second surface of the base member. The flexible wall is biased toward an extended configuration enclosing a first volume in the chamber. Further, the flexible wall is movable to a depressed configuration enclosing a second volume in the chamber less than the first volume.

In another embodiment of a medical device, a microneedle array is configured to pierce a treatment area. The medical device includes a sensor component connected to the microneedle array. Further, the medical device includes a chamber bound by a flexible wall and configured to apply a suction force to the treatment area to draw fluid into contact with the sensor component.

In another embodiment, a method for operating a medical device is provided. The method provides the medical device including a microneedle array, a base member having a first surface supporting the microneedle array and a second surface, and a flexible wall enclosing a chamber between the flexible wall and the second surface of the base member, wherein the flexible wall is biased toward an extended configuration enclosing a first volume in the chamber. The method includes piercing a treatment area with the microneedle array. Further, the method includes applying a force to depress the flexible wall to a depressed configuration enclosing a second volume in the chamber less than the first volume. The flexible wall expands to the extended configuration after the force is removed from the flexible wall.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the microneedle arrays described herein can be implemented in a variety of devices, exemplary embodiments described below are implemented in the form of medical devices, such as infusion or sensing medical devices. Many different applications for microneedle arrays described herein are possible. For example, an exemplary device may be used to pierce a patient's skin to perform sensing of fluid, such as interstitial fluid or blood. In such an embodiment, an exemplary device may be used in glucose sensing. Another exemplary device may be used to pierce a patient's skin to deliver an active agent through the skin. In certain embodiments, a device may both sense fluid through the skin and delivery an active agent through the skin.

For the sake of brevity, conventional techniques related to systems for use with microneedle arrays, such as infusion sets, insulin pumps, and the like (and the individual operating components of such systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to microneedle arrays for piercing a patient's skin. Exemplary microneedle arrays are precisely formed by progressively stamping a blank of material with a sequence of stamping dies. In an exemplary embodiment, a microneedle array is fabricated by a deep drawing process. To create deep drawn parts, a sheet of material, such as stainless steel, i.e., surgical stainless steel, or titanium or other inert and hypoallergenic materials, is first "blanked," or cut into shaped flats, such as rectangular blanks. From there, the blanks of material are fed into a stamping machine, where a hydraulically-powered punch presses the material into the desired shape via a series of progressive dies. As each blank of material moves through the die sequence, the blanks are gradually formed into the desired part shape. The deep drawing process results in seamless, one-piece parts.

Holes may be drilled into selected microneedles in the microneedle array following the drawing process. Further, excess material may be trimmed away from each microneedle array after the drawing process.

Because deep drawing is a "cold working" process, the material is automatically work hardened when form as the microneedle array. As the material is stretched and formed into the finished microneedle array, the material's grain structure is altered, giving it greater physical strength than the original base material.

Embodiments of medical devices incorporating microneedle arrays are also provided. In such medical devices, the microneedle arrays may or may not be formed according to the stamping processes described herein. Exemplary medical devices are provided with a flexible wall that encloses a chamber in fluid communication with the microneedle array. The flexible wall is biased toward an extended configuration enclosing a first volume in the chamber. During medical treatment, the flexible wall may be depressed by a force applied by a user to a depressed configuration enclosing a second volume in the chamber less than the first volume. After the force is released, the flexible wall expands to the extended configuration creating a low pressure or vacuum within the chamber.

In certain embodiments, the medical device may be used to draw fluid toward or into the medical device, such as for fluid testing or sensing. In such embodiments, the chamber is initially "empty", i.e., filled with air or other ambient gas. After depressing the flexible wall, the automatic expansion of the flexible wall back to its expanded configuration creates a low pressure within the chamber and draws fluid toward and possibly into the medical device. In exemplary embodiments, the medical device includes a testing or sensing substrate, fluid or device around, in, or behind the microneedles. As a result, movement of the flexible wall to the expanded configuration causes fluid to be drawn through the pierced skin and into contact with the testing or sensing substrate, fluid or device. In certain embodiments, the force applied by a user onto the medical device to pierce the skin with the microneedles also depresses the flexible wall such that the medical device is automatically primed for drawing fluid through the skin for testing or sensing.

For such embodiments, the disclosure relates generally to devices, systems and methods for withdrawing fluid, such as interstitial fluid or blood through the skin of a medical patient. For example, interstitial fluid glucose may diffuse from interstitial fluid into a testing or sensing area for analyte communication therein. While the fluid may be withdrawn and tested for treating diabetes, other embodiments may be employed for testing for other conditions and for other purposes. For example, further embodiments may be employed for testing for medical conditions other than diabetes.

In other embodiments, the medical device may be used to expel a fluid from the medical device and through the skin. In such embodiments, the fluid may be loaded into the chamber or in communication with the chamber such that depression of the flexible wall causes the fluid to be expelled from the medical device. For such embodiments, the disclosure relates generally to delivery devices, systems and methods for delivering media, such as a drug, to a recipient, such as a medical patient. For example such media may be provided for treating diabetes, though other embodiments may be employed for delivering media to a patient for other purposes. For example, further embodiments may be employed for delivering other types of drugs to treat diseases or medical conditions other than diabetes, including, but not limited to drugs for treating pain or certain types of cancers, pulmonary disorders or HIV. Thus, the media may be insulin, HIV drugs, drugs to treat pulmonary hypertension, iron chelation drugs, pain medications, anti-cancer treatments, medications, vitamins, hormones, or the like. Further embodiments may be employed for delivering media other than drugs, including, but not limited to, nutritional media including nutritional supplements, dyes or other tracing media, saline or other hydration media, or the like.

Perspective views of various embodiments of a microneedle array are provided in FIGS. 1-4. For example, in FIG. 1, a microneedle array 10 is provided and includes a plurality of microneedles 11 formed from and unitary with a base member 8. The base member 8 is a one-piece planar substrate having a thickness 12 and an upper surface 13. The illustrated microneedle array 10 includes eighty-eight microneedles 11 arranged symmetrically, though any suitable number of microneedles 11 may be utilized. The microneedles 11 are formed with a same, common height 14. Specifically, each microneedle 11 terminates at height 14 over the upper surface 13 of the base member 8. In an exemplary embodiment, height 14 is greater than thickness 12. In an exemplary embodiment, the height 14 of each microneedle 11 is from about 0.5 to about 2.5 millimeters (mm), for example, from about 1 to about 2 mm, such as about 1 mm.

Figure 1:
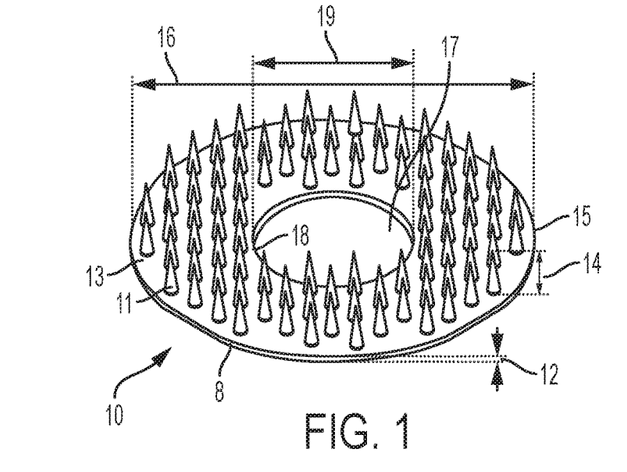
FIGS. 1-5 depict perspective views of exemplary embodiments of a microneedle array formed from a one-piece blank of material in accordance with an embodiments herein.

As shown, the base member 8 is generally circular with an outer radial edge 15 and has a diameter 16. In an exemplary embodiment, diameter 16 is from about one eighth to about one inch, such as from about ¼ to about ½ inches, for example about 5⁄16 inches. In FIG. 1, the base member 8 is formed with a center hole 17 bound by an inner radial edge 18. An exemplary center hole has a diameter 19 of from about 1⁄16 to about ¼ inches, such as about ⅛ inches.

Figure 2:
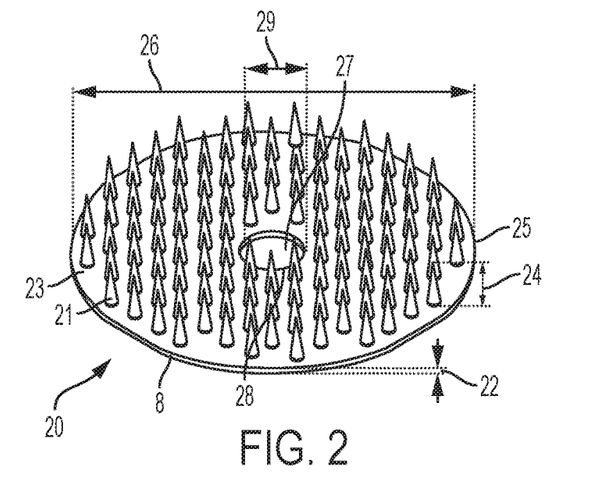

FIG. 2 illustrates another exemplary microneedle array 20. As shown, microneedle array 20 includes a plurality of microneedles 21 formed from and unitary with a base member 8. The base member 8 is a one-piece planar substrate having a thickness 22 and an upper surface 23. The illustrated microneedle array 20 includes one-hundred-eight microneedles 21 arranged symmetrically, though any suitable number of microneedles 21 may be utilized. The microneedles 21 are formed with a same, common height 24. Specifically, each microneedle 21 terminates at height 24 over the upper surface 23 of the base member 8. In an exemplary embodiment, the height 24 is greater than thickness 22. In an exemplary embodiment, the height 24 of each microneedle 21 is from about 0.5 to about 2.5 millimeters (mm), for example, from about 1 to about 2 mm, such as about 1 mm.

As shown, the base member 8 is generally circular with an outer radial edge 25 and has a diameter 26. In an exemplary embodiment, diameter 26 is from about one eighth to about one inch, such as from about ¼ to about ½ inches, for example about 5⁄16 inches. In FIG. 2, the base member 8 is formed with a center hole 27 bound by an inner radial edge 28. An exemplary center hole has a diameter 29 of from about 1⁄100 to about 1⁄10 inches, such as about 5⁄100 inches.

Figure 3:
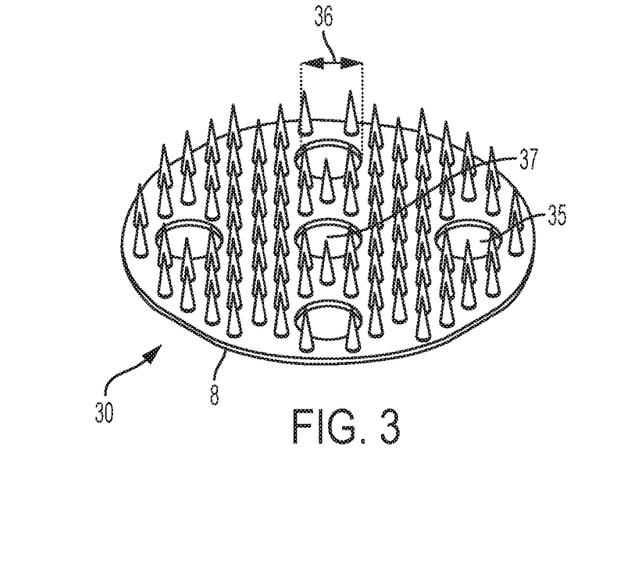

FIG. 3 illustrates a microneedle array 30 similar to microneedle array 20 of FIG. 2, but including additional radially-spaced holes 35 through the base member 8. Specifically, microneedle array 30 includes four radially-spaced holes 35 arranged symmetrically about center hole 37, i.e., at radial increments of ninety degrees. Each radially-spaced hole 35 has a common diameter 36. In FIG. 3, diameter 36 is equal to the diameter of the center hole 37. For example, the diameter 36 of each radially-spaced hole 35 may be from about 1⁄100 to about 1⁄10 inches, such as about 5⁄100 inches.

Figure 4:
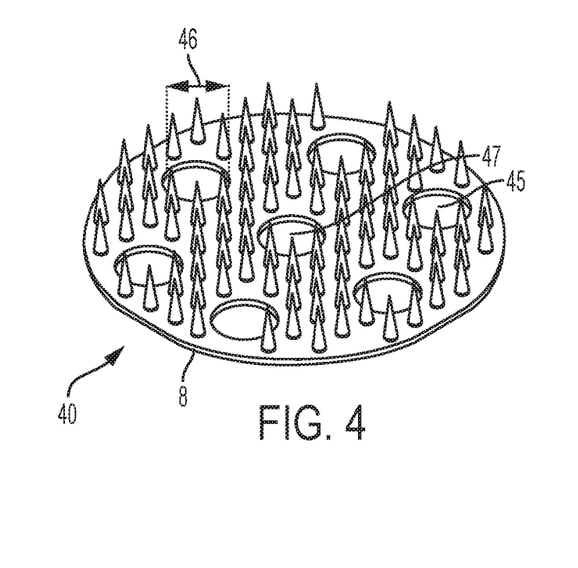

FIG. 4 illustrates a microneedle array 40 similar to microneedle array 30 of FIG. 3, but including six radially-spaced holes 45 through the base member 8. Specifically, microneedle array 40 includes six radially-spaced holes 45 arranged symmetrically about center hole 47, i.e., at radial increments of sixty degrees. Each radially-spaced hole 45 has a common diameter 46. In FIG. 4, diameter 46 is equal to the diameter of the center hole 47. For example, the diameter 46 of each radially-spaced hole 45 may be from about 1⁄100 to about 1⁄10 inches, such as about 5⁄100 inches.

Figure 5:
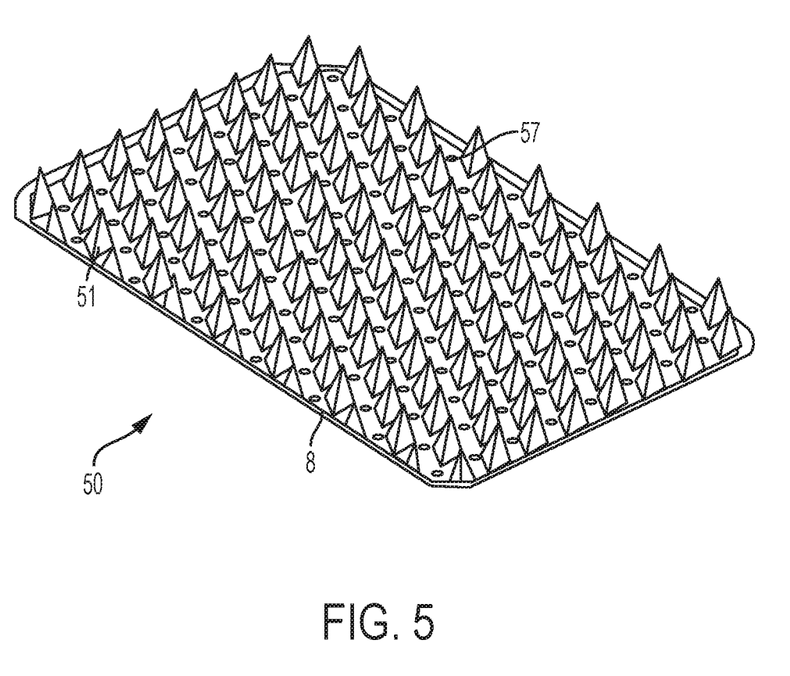

While FIGS. 1-4 illustrate microneedle arrays formed from and on generally circular base members 8 with center holes, other shapes and arrangements are contemplated. For example, FIG. 5 illustrates a microneedle array 50 having a base member 8 formed with a rounded rectangular shape. Further, base member 8 of the microneedle array 50 is perforated, i.e., formed with a plurality of holes or perforations 57. Each perforation 57 has a diameter of less than about 1⁄100 of an inch, such as from about 5⁄1000 to about 1⁄100 inches. As shown, each microneedle 51 in the microneedle array 50 is separated from each adjacent microneedle 51 by a perforation 57.

In other embodiments, the base member 8 may be formed in other shapes as desired. Further, in other embodiments, the base member 8 may be formed with any combination of center holes, radially spaced holes, and perforations, or formed without any holes and perforations.

Figure 6:
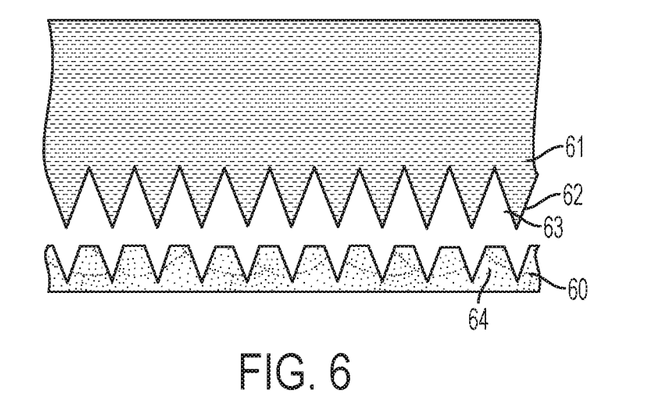
FIGS. 6-17 depict cross section schematic views during sequential stages of processing performed on a blank of material to form a microneedle array in accordance with exemplary embodiments herein.

FIGS. 6-9 illustrate a method for fabricating a microneedle array. In FIG. 6, a sheet blank of material 60 is provided. An exemplary sheet blank of material 60 is surgical stainless steel, titanium, or another suitable inert and hypoallergenic material. The sheet blank of material 60 may be introduced into a stamping machine in which a first die 61 is pushed into contact with the sheet blank of material 60. For example, a hydraulically-powered punch may press the die 61 into contact with the sheet blank of material 60. FIG. 6 illustrates the sheet blank of material 60 after the first die 61 has been pressed into and released from the sheet blank of material 60.

As shown, the die 61 includes a plurality of uniform spikes 62 separated by troughs or root relief regions 63. In an exemplary embodiment, each spike 62 is formed with an angle of sixty degrees. In FIG. 6, the spikes 62 are pushed into, but not through the sheet blank of material 60. As a result, regions 64 of the sheet blank of material 60 are drawn up into the troughs 63.

Figure 7:
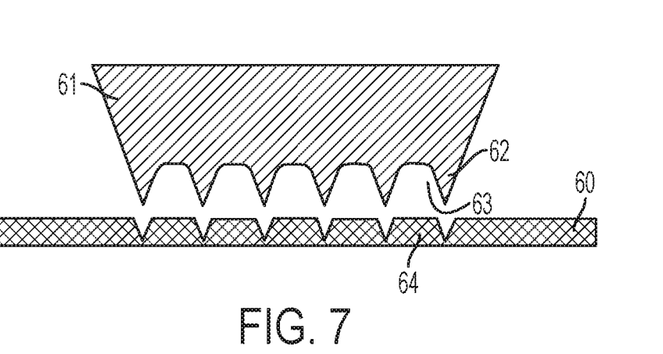
Figure 8:
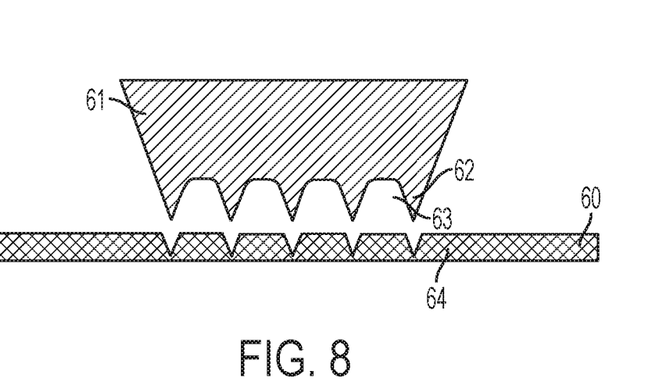

FIG. 6 is a cross section view illustrating the sheet blank of material 60 where multiple lines of microneedles will be formed. In adjacent lines therein, the microneedles will be formed at an offset. This is depicted in FIGS. 7 and 8 which provide isolated views of adjacent lines of spikes 62 in FIG. 6. Thus, the view of the die 61 in FIGS. 7 and 8 illustrate how adjacent lines of microneedles are formed in the sheet blank of material 60. As shown, spikes 62 in one line may be aligned with the troughs 63 in an adjacent line. This embodiment may be considered to be a skip toothed method.

Figure 9:
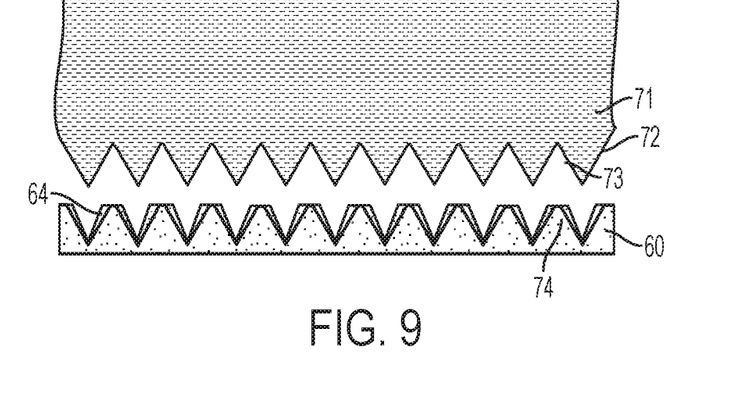

Referring now to FIG. 9, further processing of the sheet blank of material 60 is described. In FIG. 9, a second die 71 is pushed into contact with the sheet blank of material 60. For example, the sheet blank of material 60 may be removed from the location of the first die 61 and positioned for contact with the second die 71. Then, a hydraulically-powered punch may press the die 71 into contact with the sheet blank of material 60. FIG. 9 illustrates the sheet blank of material 60 after the die 71 has been pressed into and released from the sheet blank of material 60.

As shown, the die 71 includes a plurality of uniform spikes 72 separated by troughs or root relief regions 73. In an exemplary embodiment, each spike 72 is formed with an angle of forty-five degrees. In FIG. 9, the spikes 72 are pushed into, but not through the sheet blank of material 60. As a result, regions 74 of the sheet blank of material 60 are drawn further up into the troughs 73. FIG. 9 illustrates the former location of the regions 64 of the sheet blank of material 60 after processing with the first die 61 and before processing with the second die 71 to demonstrate the effect of the second die 71.

Figure 10:
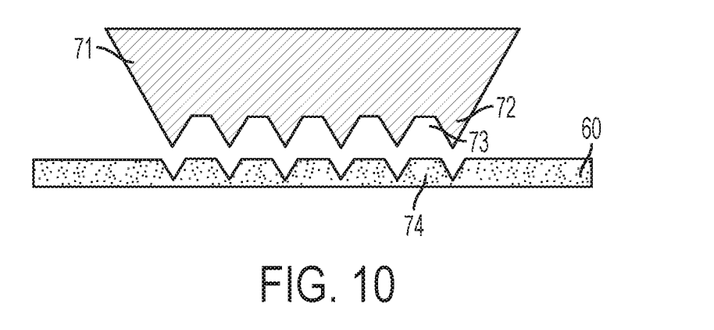
Figure 11:
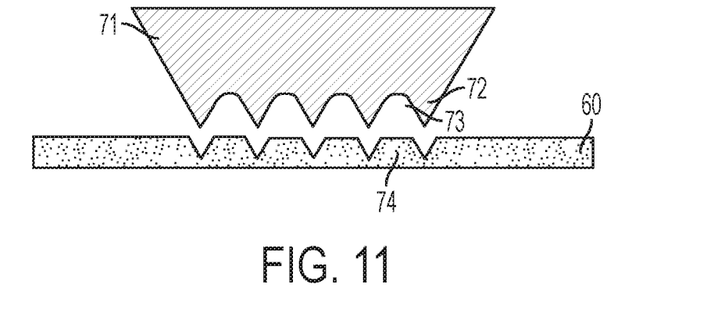

FIG. 9 is a cross section view illustrating the sheet blank of material 60 where multiple lines of microneedles will be formed. In adjacent lines therein, the microneedles will be formed at an offset. This is depicted in FIGS. 10 and 11 which provide isolated views of adjacent lines of spikes 72 in FIG. 9. Thus, the view of the die 71 in FIGS. 10 and 11 illustrate how adjacent lines of microneedles are formed in the sheet blank of material 60. As shown, spikes 72 in one line may be aligned with the troughs 73 in an adjacent line. As described above, this embodiment may be considered to be a skip toothed method.

Figure 12:
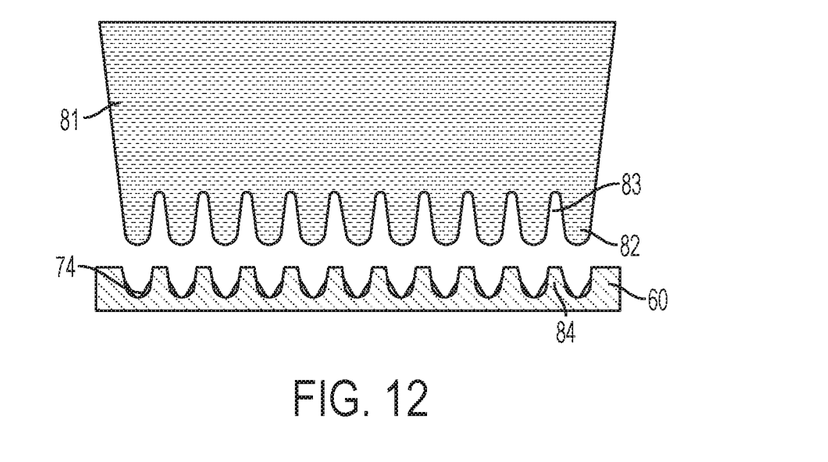

Referring now to FIG. 12, further processing of the sheet blank of material 60 is described. In FIG. 12, a third die 81 is pushed into contact with the sheet blank of material 60. For example, the sheet blank of material 60 may be removed from the location of the die 71 and positioned for contact with the die 81. Then, a hydraulically-powered punch may press the die 81 into contact with the sheet blank of material 60. FIG. 12 illustrates the sheet blank of material 60 after the die 81 has been pressed into and released from the sheet blank of material 60.

As shown, the die 81 includes a plurality of uniform spikes 82 separated by troughs or root relief regions 83. In an exemplary embodiment, each spike 82 is formed with rounded tip. In an exemplary embodiment, each spike 82 is formed with an angle of from about twenty to about thirty degrees. In FIG. 12, the spikes 82 are pushed into, but not through the sheet blank of material 60. As a result, regions 84 of the sheet blank of material 60 are drawn further up into the troughs 83. FIG. 12 illustrates the former location of the regions 74 of the sheet blank of material 60 after processing with the die 71 and before processing with the die 81 to demonstrate the effect of the die 81.

Figure 13:
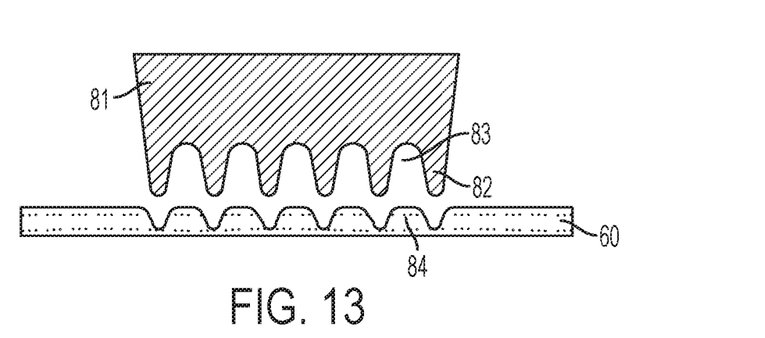
Figure 14:
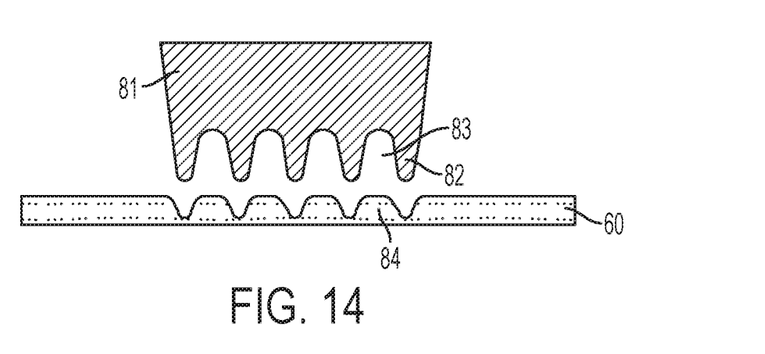

FIG. 12 is a cross section view illustrating the sheet blank of material 60 where multiple lines of microneedles will be formed. In adjacent lines therein, the microneedles will be formed at an offset. This is depicted in FIGS. 13 and 14 which provide isolated views of adjacent lines of spikes 82 in FIG. 12. Thus, the view of the die 81 in FIGS. 13 and 14 illustrate how adjacent lines of microneedles are formed in the sheet blank of material 60. As shown, spikes 82 in one line may be aligned with the troughs 83 in an adjacent line. This embodiment may be considered to be a skip toothed method.

Figure 15:
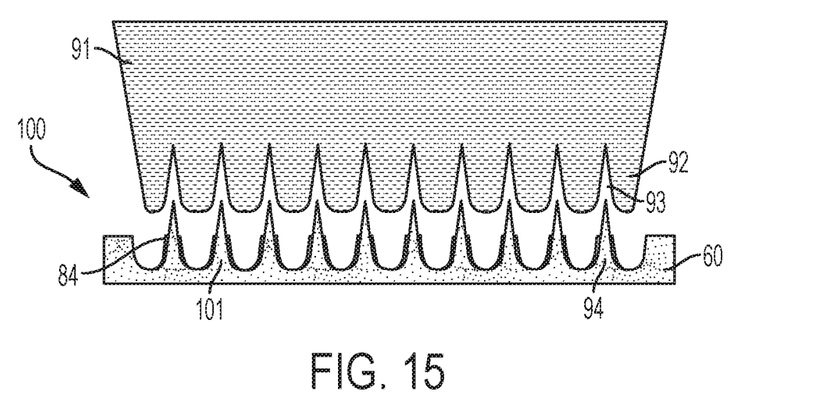

Referring now to FIG. 15, further processing of the sheet blank of material 60 is described. In FIG. 15, a fourth die 91 is pushed into contact with the sheet blank of material 60. For example, the sheet blank of material 60 may be removed from the location of the die 81 and positioned for contact with the die 91. Then, a hydraulically-powered punch may press the die 91 into contact with the sheet blank of material 60. FIG. 12 illustrates the sheet blank of material 60 after the die 91 has been pressed into and released from the sheet blank of material 60.

As shown, the die 91 includes a plurality of uniform spikes 92 separated by troughs or root relief regions 93. In an exemplary embodiment, each spike 92 is formed with rounded tip. In an exemplary embodiment, each spike 92 is formed with an angle of from about ten to about fifteen degrees. In FIG. 15, the spikes 92 are pushed into, but not through the sheet blank of material 60. As a result, regions 94 of the sheet blank of material 60 are drawn further up into the troughs 93. FIG. 15 illustrates the former location of the regions 84 of the sheet blank of material 60 after processing with the die 81 and before processing with the die 91 to demonstrate the effect of the die 91.

Figure 16:
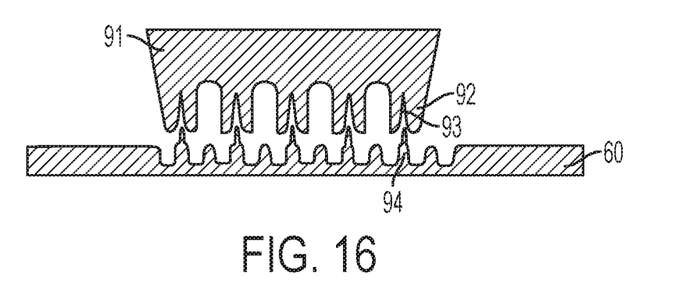
Figure 17:
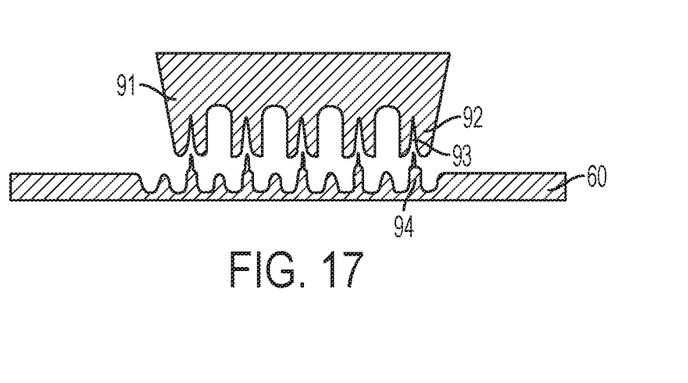

FIG. 15 is a cross section view illustrating the sheet blank of material 60 where multiple lines of microneedles will be formed. In adjacent lines therein, the microneedles will be formed at an offset. This is depicted in FIGS. 16 and 17 which provide isolated views of adjacent lines of spikes 92 in FIG. 15. Thus, the view of the die 91 in FIGS. 16 and 17 illustrate how adjacent lines of microneedles are formed in the sheet blank of material 60. As shown, spikes 92 in one line may be aligned with the troughs 93 in an adjacent line. This embodiment may be considered to be a skip toothed method.

While the method may utilize any number of dies to form the desired shapes of microneedles, FIG. 15 illustrates the final press process and formation of a microneedle array 100 including the desired microneedles 101. In certain embodiments, fewer or additional dies may be used to perform the deep drawing process to form the blank sheet of material into the desired microneedle array shape. Herein, a progression of four dies is illustrated to displace the material into the microneedle array.

Figure 18:
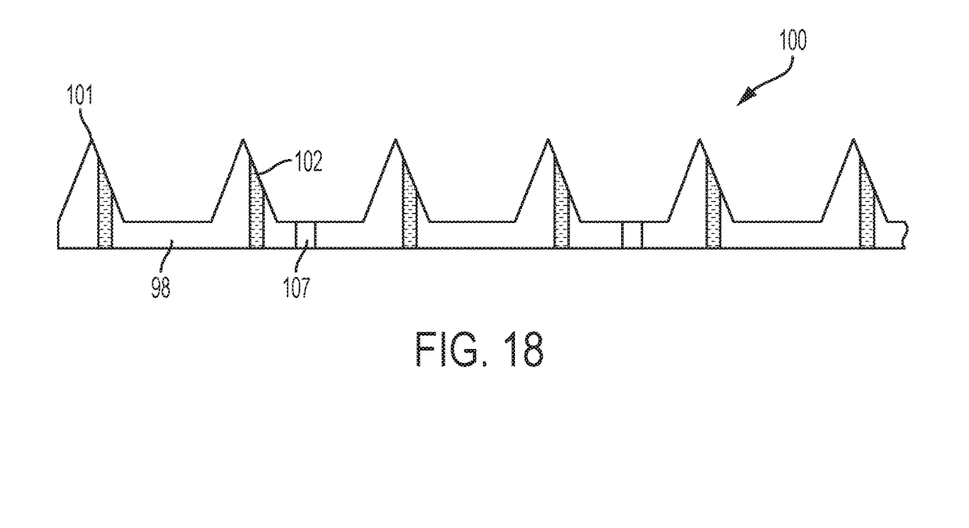
FIG. 18 depicts a cross section schematic view of a microneedle array in accordance with an exemplary embodiment herein.

The method may continue by performing non-stamping processes on the microneedle array 100 and sheet blank of material 60. For example, the method may include drilling a hole through selected microneedles in the microneedle array. In an exemplary embodiment, holes may be drilled by an electrical discharge machining (EDM) process. For example, in FIG. 18, a sheet blank of material is stamped to form a microneedle array 100 and base member 98. As shown, the base member 98 is formed with perforations 107. Further, holes 102 are formed through selected microneedles 101 in the microneedle array 100.

Figure 19:
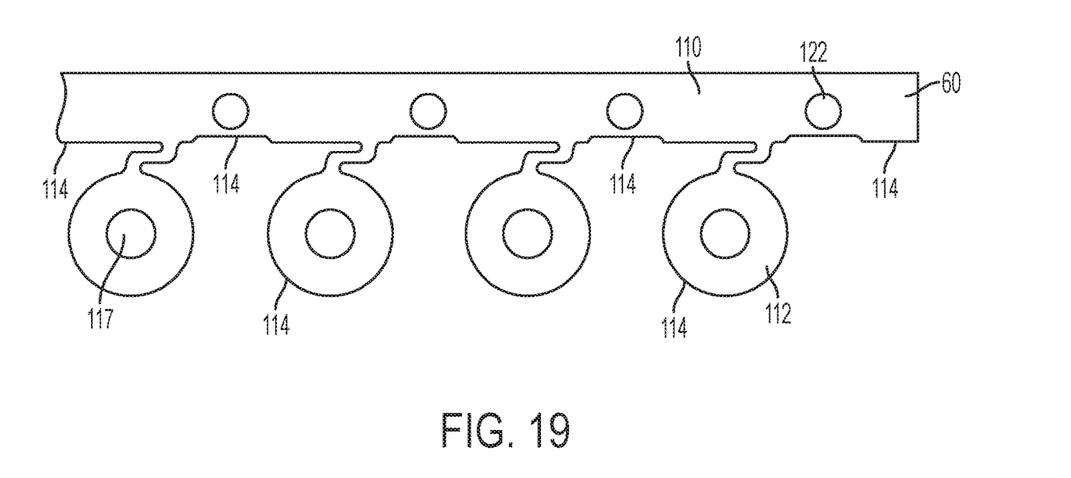
FIG. 19 is an overhead view of a blank of material after processing to form four microneedle array regions thereon in accordance with exemplary embodiments herein.

Other processing may include cleaning and packaging. Further, microneedle arrays could be removed from the sheet blank of material. Referring now to FIG. 19, preparation of the sheet blank of material 60 before the microneedle stamping process is described. In FIG. 19, the sheet blank of material 60 is cut into a carrier strip 110 and microneedle array regions 112 connected to the carrier strip 110. For example, an initial stamping process may be performed to cut the sheet blank of material 60 along the perimeter 114 to define and form the microneedle array regions 112, i.e., the regions of the sheet blank of material 60 where the microneedle arrays will be formed. Further, preparation of the sheet blank of material 60 may include piercing the microneedle array regions 112 to form center holes 117 therethrough. While not illustrated, preparation of the sheet blank of material 60 may include piercing the microneedle array regions 112 to form the radially-spaced holes therethrough. Further, preparation of the sheet blank of material 60 may include perforating the microneedle array regions 112 to form perforations (not shown) therethrough. Also, apertures 122 for alignment or placement of the carrier strip 110 during stamping may be formed in the carrier strip 110 as shown.

After formation of the microneedle arrays 100 in the microneedle array regions 112, according to the processing of FIGS. 6-17, the microneedle array regions 112 may be separated from the carrier strip 110, such as during packaging.

Figure 20:
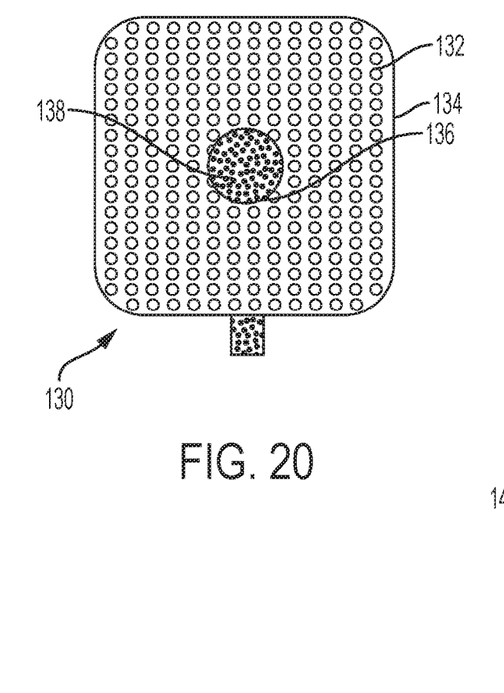
FIGS. 20-22 are plan views of the microneedle array surface of medical devices incorporating embodiments of a microneedle array.
Figure 21:
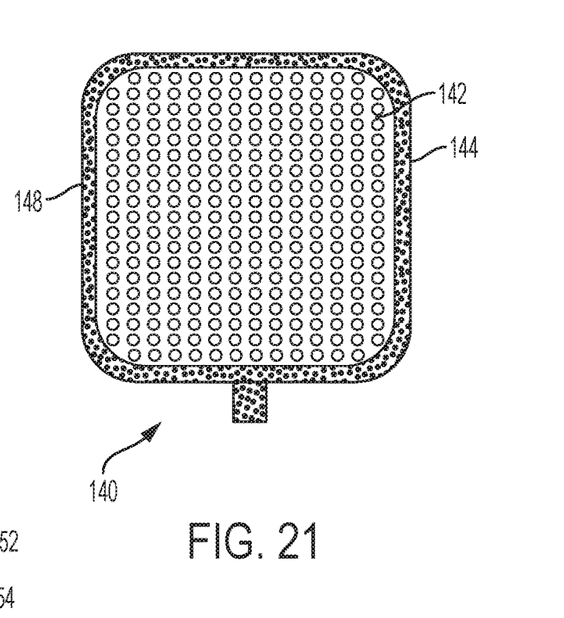
Figure 22:
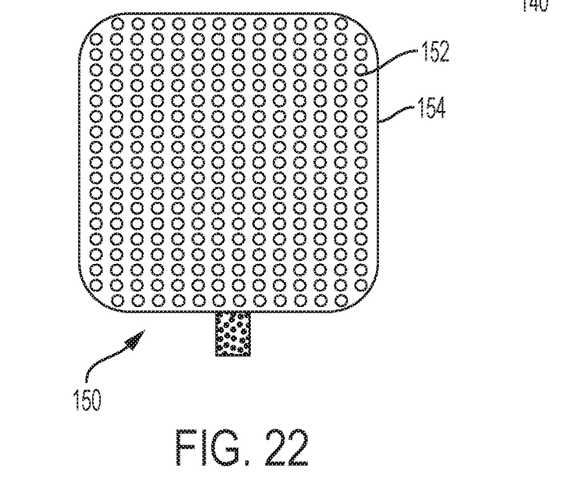

Referring now to FIGS. 20-22, embodiments of a medical device incorporating a microneedle array are described. As noted above, the microneedle arrays may be formed with center holes, radially-spaced holes, and perforations formed in the sheet blank of material 60 and/or with holes drilled through the microneedles themselves. In FIG. 20, an embodiment of a medical device 130 includes a microneedle array 132 including microneedles extending from a base member 134. A center hole 136 is formed in the base member 134. A sensor component 138, such as a testing or sensing substrate, fluid or device, may be located in the center hole 136, or behind the base member 134 such that the center hole exposes the sensor component 138. An exemplary sensor component 138 is a test strip such as a strip of glucose paper for reading by a glucose meter. During use the microneedles may pierce the skin and cause fluid to collect and come into contact with the sensor component 138. If the sensor component 138 is located behind the base member 134, then perforations through the base member 134 or holes through the microneedles themselves may further allow for fluid to pass through the base member 134 and contact the sensor component 138.

In FIG. 21, an embodiment of a medical device 140 includes a microneedle array 142 including microneedles extending from a base member 144. A sensor component 148, such as a testing or sensing substrate, fluid or device, may be located around the periphery of the base member 144 or behind the base member 144 such that the sensor component 148 extends beyond the periphery of the base member 144. An exemplary sensor component 148 is a test strip such as a strip of glucose paper for reading by a glucose meter. During use the microneedles may pierce the skin and cause fluid to collect and come into contact with the sensor component 148. If the sensor component 148 is located behind the base member 144, then perforations through the base member 144 or holes through the microneedles themselves may further allow for fluid to pass through the base member 144 and contact the sensor component 148.

FIG. 22 depicts an embodiment of a medical device 150 including a microneedle array 152 with microneedles extending from a base member 154. A sensor component (not visible), such as a testing or sensing substrate, fluid or device, is located behind the base member 154. An exemplary sensor component is a test strip such as a strip of glucose paper for reading by a glucose meter. Selected microneedles include holes therethrough. During use, the microneedles may pierce the skin and cause fluid to collect, pass through the holes in the microneedles and come into contact with the sensor component. Additionally or alternatively, the base member 154 may be perforated to allow the fluid to pass through the base member 154 and contact the sensor component.

Figure 23:
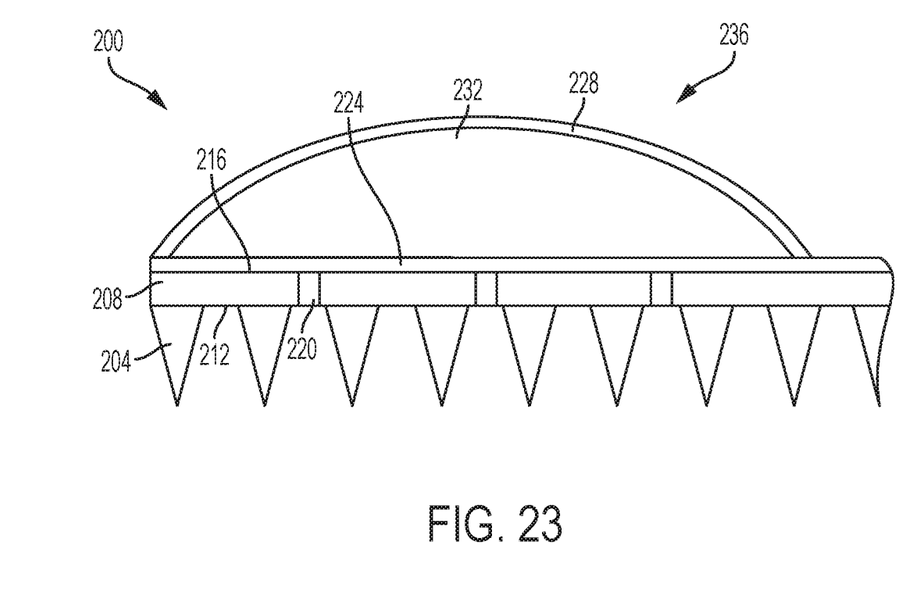
FIGS. 23-26 depict a cross section schematic view of a medical device incorporating a microneedle array during sequential stages of medical treatment of a patient in accordance with exemplary embodiments herein.

FIGS. 23-26 illustrate an embodiment and use of another medical device 200 incorporating a microneedle array 204. In FIG. 23, microneedle array 204 is formed on a base member 208. An exemplary base member 208 is a one-piece planar substrate having a surface 212, a surface 216 and a thickness therebetween. As shown, the microneedles of the microneedle array 204 are formed on and extend from surface 212 of the base member 208. In an exemplary embodiment, the microneedles are formed from and unitary with the base member 208. Further, exemplary microneedles terminate at a distance from surface 212 that is greater than the thickness of the base member 208. As further shown, holes, openings, or perforations 220 are formed in and pass through the base member 208 from surface 212 to surface 216.

The illustrated medical device 200 further includes a sensor component 224 located adjacent the surface 216 of the base member 208. An exemplary sensor component 224 is a porous chemical test strip, such as a strip of glucose paper for reading by a glucose meter.

Also, the illustrated medical device 200 includes a flexible wall 228 enclosing a chamber 232 between the flexible wall 228 and the second surface 216 of the base member 208. More specifically, in the embodiment of FIG. 23, the flexible wall 228 encloses a chamber 232 between the flexible wall 228 and the sensor component 224. The flexible wall 228 is biased toward an extended configuration 236 (illustrated in FIG. 23) enclosing a first volume in the chamber 232. In an exemplary embodiment, the flexible wall 228 is a spherical dome. An exemplary flexible wall 228 is an elastomeric material.

Figure 24:
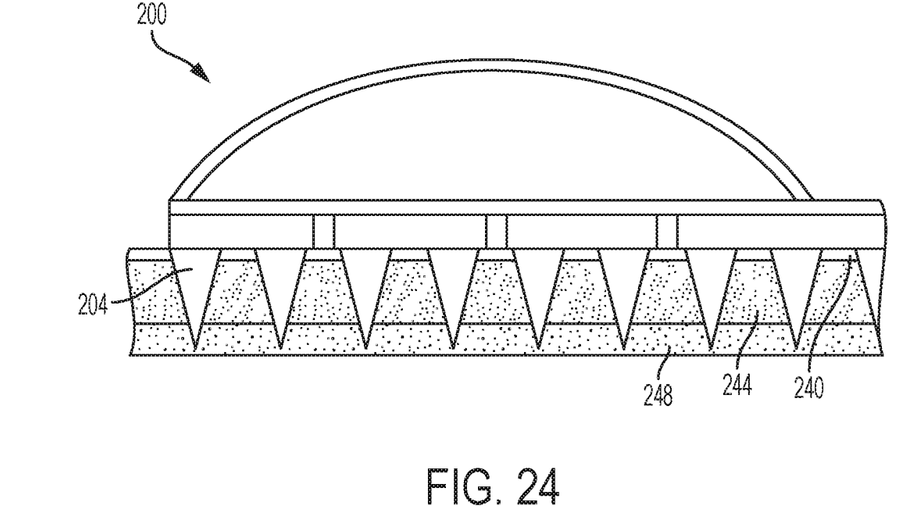

Referring now to FIG. 24, the medical device 200 is contacted to a patient's skin 240 such that the microneedles of the microneedle array 204 are inserted through the epidural layers 244 and into the subcutaneous fluid 248.

Figure 25:
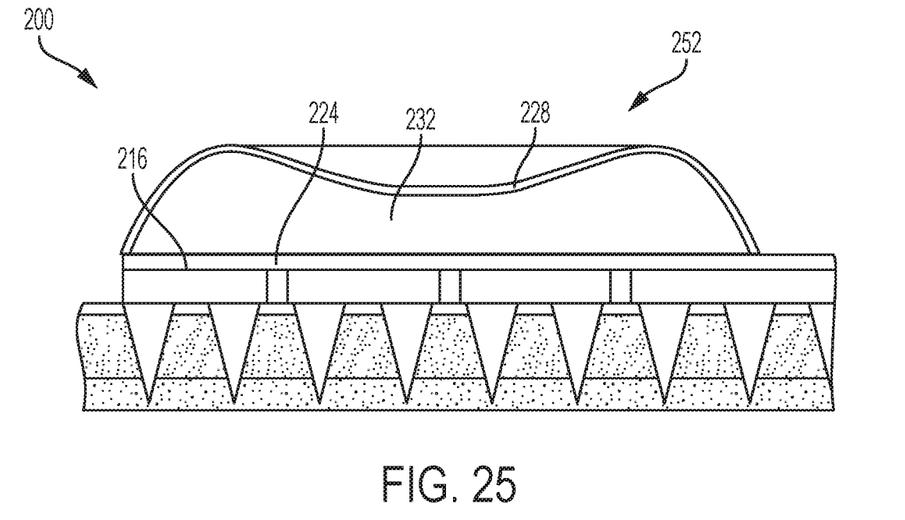

In FIG. 25, the flexible wall 228 is depressed and moved to a depressed configuration 252 enclosing a second volume in the chamber 232 less than the first volume. The flexible wall 228 may be depressed by a user when pushing the flexible wall 228 to cause the microneedles of the microneedle array 204 to pierce the skin. For example, a force needed to pierce the skin with the microneedle array 204 may cause the flexible wall 228 to move to the depressed configuration 252 in which the volume of the chamber 232 is reduced.

Figure 26:
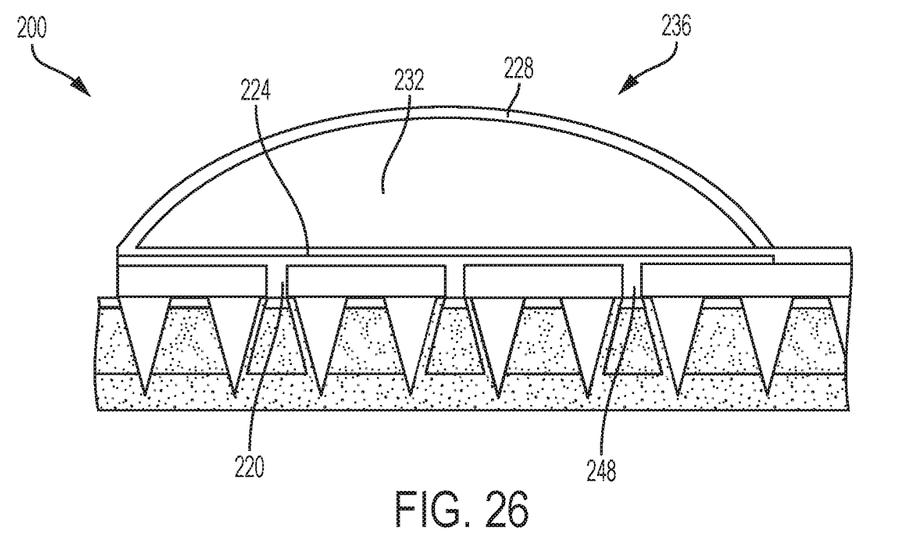

In FIG. 26, the downward force on the flexible wall 228 is released. As a result, the flexible wall 228 returns to the extended configuration 236, expanding the chamber 232 to the first volume. Therefore, a low pressure is created within the chamber 232. The low pressure within the chamber 232 causes a suction force to draw subcutaneous fluid 248 through the holes 220 and into contact with the sensor component 224.

Therefore, the medical device of FIGS. 23-26 is provided with the capability of drawing fluid through a patient's skin and into contact with a sensor component. In other embodiments, the chamber 232 may be filled with a fluid such as a drug or other medicament and the microneedle array 204 may be formed with openings or holes in selected microneedles. Thus, depressing the flexible wall 228 may cause the fluid contained within the chamber 232 to be expelled from the holes in the selected microneedles. In this manner, a fluid may be delivered into a patient through the patient's skin via the microneedle array.

The subject matter described herein is not limited to any type of fluid drawn into a medical device for sensing or to any type of fluid expelled from a medical device for treatment. For example, flowable solids, liquids or gels may be expelled from the medical device for treatment. In certain embodiments, solid, liquid, or gel formats of insulin may be applied.

Further, it is noted that while embodiments herein have been described with holes or apertures through the microneedles and/or through the base member, the microneedle array need not be formed with any holes or apertures for passing media such as flowable solids, liquids or gels therethrough. For example, rather than applying media from the backside of the microneedle array to a treatment area through holes in the microneedle array, the media may be provided on the frontside, i.e., needle side, of the microneedle array. Therefore, the microneedles may pierce the skin and the media may contact fluids such as interstitial fluids or blood for treatment. In certain embodiments, the media may be in the form of solid, liquid, or gel and need not be flowable as prepared on the frontside of the microneedle array.

In other embodiments, the microneedle array may include holes through the microneedles and/or base member as well as media applied to the frontside of the microneedle array. In such embodiments media can also be applied from the backside of the microneedle array through the holes, or the holes may be used to apply a low pressure regime to draw fluid toward and possibly into the medical device as described above.

For the sake of brevity, conventional techniques related to glucose or other fluid sensing and/or monitoring, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A medical device comprising:
   a microneedle array;
   a base member having a first surface supporting the microneedle array and a second surface, wherein the base member includes inter-needle regions wherein the first surface is not covered with a microneedle from the microneedle array, and wherein the base member is perforated with holes extending from the first surface through the second surface in the inter-needle regions; and
   a flexible wall enclosing a chamber between the flexible wall and the second surface of the base member, wherein the flexible wall is biased toward an extended configuration enclosing a first volume in the chamber, wherein the flexible wall is movable to a depressed configuration enclosing a second volume in the chamber less than the first volume.

2. The medical device of claim 1 further comprising a sensor component between the base member and the flexible wall.

3. The medical device of claim 2 wherein the sensor component covers the second surface of the base member and is porous.

4. The medical device of claim 1 wherein microneedles in the microneedle array are solid and do not include holes therethrough.

5. The medical device of claim 1 wherein the microneedle array and the first surface of the base member form a front side of the medical device, wherein the medical device further comprises solid, liquid, or gel media on the front side of the medical device, and wherein the media is selected from insulin, medications, vitamins, hormones, nutritional media, tracing media, or hydration media.

6. The medical device of claim 1 wherein the flexible wall is a spherical dome.

7. The medical device of claim 1 wherein the microneedle array surrounds an opening, and wherein the medical device further comprises a sensor component located in the opening and supported by the first surface of the base member.

8. The medical device of claim 1 further comprising a sensor component supported by the first surface of the base member and at least partially surrounding the microneedle array.

9. The medical device of claim 1 wherein a selected microneedle in the microneedle array is formed with a hole extending from an exterior surface of the selected microneedle to an interior surface of the selected microneedle.

10. A medical device comprising:
    a microneedle array configured to pierce a treatment area;
    a base member having a first surface supporting the microneedle array and a second surface;
    a sensor component on the first surface of the base member; and
    a chamber connected to the second surface of the base member, wherein the chamber is bound by a flexible wall and configured to apply a suction force to the treatment area.

11. The medical device of claim 10 wherein the microneedle array surrounds an opening, and wherein the sensor component is located in the opening.

12. The medical device of claim 10 wherein the microneedle array has a periphery, wherein the first surface of the base member includes a peripheral region extending from the periphery of the microneedle array to an outer edge, and wherein the sensor component is located on the peripheral region of the base member and surrounds the microneedle array.

13. A method for operating a medical device, the method comprising:
    providing the medical device comprising:
        a microneedle array;
        a base member having a first surface supporting the microneedle array and a second surface;
        a flexible wall enclosing a chamber between the flexible wall and the second surface of the base member, wherein the flexible wall is biased toward an extended configuration enclosing a first volume in the chamber; and
        a fluid contained in the chamber, wherein the fluid is selected from insulin, medications, vitamins, hormones, nutritional media, tracing media, or hydration media;
    piercing a treatment area with the microneedle array; and
    applying a force to depress the flexible wall to a depressed configuration enclosing a second volume in the chamber less than the first volume and expelling the fluid onto and/or into the treatment area.

14. The method of claim 13 wherein the base member includes inter-needle regions wherein the first surface is not covered with a microneedle from the microneedle array, wherein the base member is perforated with holes extending from the first surface through the second surface in the inter-needle regions; and wherein expelling the fluid onto and/or into the treatment area comprises expelling the fluid through the holes in the inter-needle regions.

15. The method of claim 13 wherein a selected microneedle in the microneedle array is formed with a hole extending from an exterior surface of the selected microneedle to an interior surface of the selected microneedle, and wherein applying the force to depress the flexible wall to the depressed configuration comprises expelling the fluid from the chamber and through the hole in the selected microneedle.

16. The method of claim 13 wherein the flexible wall expands to the extended configuration after the force is removed from the flexible wall causing a body fluid to be drawn from the treatment area and to the medical device.

17. The method of claim 16 wherein the medical device further comprises a sensor component between the base member and the flexible wall, and wherein when the flexible wall expands to the extended configuration after the force is removed from the flexible wall the body fluid is drawn from the treatment area and into contact with the sensor component.

18. The method of claim 13 wherein the microneedle array has a periphery, wherein the first surface of the base member includes a peripheral region extending from the periphery of the microneedle array to an outer edge, and wherein the medical device further comprises a sensor component located on the peripheral region of the base member and surrounding the microneedle array.

19. The method of claim 13 wherein the microneedle array surrounds an opening, wherein the medical device further comprises a sensor component located in the opening and supported by the first surface of the base member, and wherein the medical device further comprises a sensor component supported by the first surface of the base member and at least partially surrounding the microneedle array.

20. The method of claim 13 wherein the medical device further comprises a sensor component supported by the first surface of the base member and at least partially surrounding the microneedle array, and wherein when the flexible wall expands to the extended configuration after the force is removed from the flexible wall a fluid is drawn from the treatment area and into contact with the sensor component.

* * * * *